United States Patent [19]

Takatsu et al.

[11] 4,455,443
[45] Jun. 19, 1984

[54] NEMATIC HALOGEN COMPOUND

[75] Inventors: Haruyoshi Takatsu, Kodaira; Hisato Sato, Tokyo, both of Japan

[73] Assignees: Dainippon Inc.; Chemicals, Inc., both of Tokyo, Japan

[21] Appl. No.: 413,798

[22] Filed: Sep. 1, 1982

[30] Foreign Application Priority Data

Sep. 10, 1981 [JP] Japan .................. 56-141728
Sep. 10, 1981 [JP] Japan .................. 56-141730
Jul. 8, 1982 [JP] Japan .................. 57-117848

[51] Int. Cl.$^3$ .................. C09K 3/34; G02F 1/13; C07C 25/18
[52] U.S. Cl. .................. 570/129; 570/182; 252/299.5; 252/299.63; 350/350 R
[58] Field of Search .................. 570/129, 182; 252/299.63, 299.5

[56] References Cited

U.S. PATENT DOCUMENTS

| | | | |
|---|---|---|---|
| 4,035,056 | 7/1977 | Coates et al. | 252/299.63 |
| 4,261,651 | 4/1981 | Gray et al. | 252/299.63 |
| 4,302,352 | 11/1981 | Eidenschink et al. | 252/299.63 |
| 4,340,498 | 7/1982 | Sugimori | 252/299.5 |
| 4,386,007 | 5/1983 | Krause et al. | 252/299.62 |
| 4,400,293 | 8/1983 | Römer | 252/299.63 |
| 4,415,470 | 11/1983 | Eidenschink | 252/299.5 X |

FOREIGN PATENT DOCUMENTS

| | | | |
|---|---|---|---|
| 51738 | 5/1982 | European Pat. Off. | 252/299.63 |
| 3139130 | 5/1982 | Fed. Rep. of Germany | 252/299.63 |
| 148184 | 11/1979 | Japan | 252/299.63 |
| 50935 | 3/1982 | Japan | 252/299.63 |
| 64645 | 4/1982 | Japan | 252/299.63 |
| 95933 | 6/1982 | Japan | 252/299.66 |
| 2086385 | 5/1982 | United Kingdom | 252/299.63 |
| 2092146 | 8/1982 | United Kingdom | 252/299.01 |

OTHER PUBLICATIONS

Pracfcke, ". . . Flüssigkristalline Verbindurgen", Chemiker–Zeiturg, 104, Jahrgang (1980), Nr. 9.

Primary Examiner—Teddy S. Gron
Assistant Examiner—Catherine S. Kilby
Attorney, Agent, or Firm—Sherman & Shalloway

[57] ABSTRACT

A compound of the formula

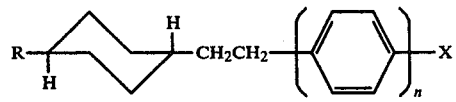

wherein R represents a linear alkyl group having 1 to 7 carbon atoms, n represents an integer of 1 or 2, and X represents F when n is 1 and F or Cl when n is 2.

15 Claims, 6 Drawing Figures

NEMATIC HALOGEN COMPOUND

This invention relates to novel nematic halogen compounds useful as electro-optical display materials. More specifically, it relates to 1-cyclohexyl-2-phenylethane derivatives and 1-cyclohexyl-2-biphenylethane derivatives.

The novel nematic liquid crystals provided by this invention are trans(equatorial-equatorial)-4-n-alkylcyclohexylethane derivatives represented by the general formula wherein R represents a liner alkyl group having 1 to 7 carbon atoms, n represents an integer of 1 or 2, and X represents F when n is 1 and F or Cl when n is 2.

Typical liquid crystal display cells include a field effect mode cell proposed by M. Schadt et al. [Applied Physics Letters, 18, 127–128 (1971)], a dynamic scattering mode cell proposed by G. H. Heilmeier et al. [Proceedings of the I.E.E.E., 56, 1162–1171 (1968)], and a guest-host mode cell proposed by G. H. Heilmeier [Applied Physics Letters, 13, 91 (1968)] or D. L. White [Journal of Applied Physics, 45, 4718 (1974)].

Compounds of formula (I) in which n is 1, i.e. 1-cyclohexyl-2-phenylethane derivatives, have a low viscosity, and therefore, can effectively reduce the viscosities of various nematic liquid crystalline materials when mixed with them.

Many of the compounds used heretofore as viscosity reducing agents are compounds having weak negative dielectric anisotropy, such as 4-alkyl-4'-alkylphenylcyclohexanes of the formula wherein R and R' are alkyl groups, or 4-alkylcyclohexyl-4'-alkylcyclohexanecarboxylates of the formula wherein R and R' are alkyl groups. Hence, these compounds have the defect that when mixed with various other nematic liquid crystalline materials, they reduce the dielectric anisotropy of the materials. Consequently, driving of field effect mode cells at low voltages, which is one important problem in the art, is difficult. Compounds of formula (I) in which n is 1, i.e. 1-cyclohexyl-2-phenylethane derivatives, are novel compounds having weak positive dielectric anisotropy and therefore being free from the aforesaid defect. Specifically, in the preparation of mixed liquid crystals having the desired viscosity by mixing with at least one other nematic liquid crystalline compound, the aforesaid known viscosity reducing agents reduce the dielectric anisotropy of the mixed liquid crystals, but the compounds of formula (I) in which n is 1 increase their dielectric anisotropy or minimize its reduction.

Compounds of formula (I) in which n is 2, i.e. 1-cyclohexyl-2-biphenylethane derivatives, are liquid crystalline compounds having a low viscosity and a high nematic phase to isotropic liquid phase transition temperature (N—I point). The possession of a nematic phase over a broad temperature range including room temperature is an important property required of all display cells in common. Many materials having such a property and practical utility are prepared by mixing at least one compound having a nematic phase at room temperature and at least one compound having a nematic phase at temperatures higher than room temperature. Many of the aforesaid mixed liquid crystals now in commercial use are required to have a nematic phase at least over an entire temperature range of from −30° to +65° C. In order to meet this requirement, it is often the practice to use compounds having a crystalline phase to nematic phase transition temperature (C—N point) of about 100° C. and a nematic phase-isotropic liquid phase transition temperature (N—I point) of about 200° C., such as 4,4'-substituted terphenyl, 4,4'-substituted biphenylcyclohexane, or phenyl 4,4'-substituted benzoyloxybenzoate, as the compound having a nematic phase at temperatures higher than room temperature. However, when these compounds are mixed in amounts sufficient to adjust the N—I point of the mixed crystals to 65° C. or higher, they undesirably increase the viscosity of the resulting mixed crystals and therefore retard their response speed.

The compounds of formula (I) in which n is 2, i.e. 1-cyclohexyl-2-biphenylethane derivatives, in accordance with this invention are novel compounds free from this property. Specifically, in the preparation of mixed liquid crystals having an N—I point of at least 65° C. and practical utility by mixing at least one other nematic liquid crystalline compound, the known liquid crystalline compounds mentioned above greatly increase the viscosity of the resulting mixed crystals, but these compounds of the invention reduce the viscosity of the mixed crystals or limit its increase to a small extent.

The compounds of formula (I) in accordance with this invention can be produced, for example, according to the reaction scheme given below (in which R, X and n are as defined above), by first reacting a p-halobenzene or p-halobiphenyl with a compound of formula (II) and anhydrous aluminum chloride in carbon disulfide or nitrobenzene to form a compound of formula (III), and then reacting the compound of formula (III) with hydrazine and potassium hydroxide in diethylene glycol or triethylene glycol.

(I)

Table 1 summarizes the transition temperatures of typical examples of the compounds of formula (I) produced as above. In the table, C stands for a crystalline phase; N, for a nematic phase; and I, for an isotropic liquid phase.

TABLE 1

| No. | n | R | X | Transition temperature (°C.) |
|---|---|---|---|---|
| 1 | 1 | n-$C_3H_7$— | F | 5(C → I) −25(I ⇌ N) |
| 2 | 1 | n-$C_4H_9$— | F | 7(C → I) −28(I ⇌ N) |
| 3 | 1 | n-$C_5H_{11}$— | F | 9(C → I) −8(I ⇌ N) |
| 4 | 1 | n-$C_6H_{13}$— | F | 12(C → I) −11(I ⇌ N) |
| 5 | 1 | n-$C_7H_{15}$— | F | 13(C → I) −1(I ⇌ N) |
| 6 | 2 | $C_2H_5$— | F | 68(C ⇌ N) 96(N ⇌ I) |
| 7 | 2 | n-$C_3H_7$— | F | 76(C ⇌ N) 125(N ⇌ I) |
| 8 | 2 | n-$C_4H_9$— | F | 69(C ⇌ N) 113(N ⇌ I) |
| 9 | 2 | n-$C_5H_{11}$— | F | 82(C ⇌ N) 121(N ⇌ I) |
| 10 | 2 | n-$C_6H_{13}$— | F | 75(C ⇌ N) 109(N ⇌ I) |
| 11 | 2 | n-$C_7H_{15}$— | F | 87(C ⇌ N) 119(N ⇌ I) |
| 12 | 2 | n-$C_3H_7$— | Cl | 100(C ⇌ N) 158(N ⇌ I) |
| 13 | 2 | n-$C_5H_{11}$— | Cl | 110(C ⇌ N) 152(N ⇌ I) |
| 14 | 2 | n-$C_7H_{15}$— | Cl | 114(C ⇌ N) 147(N ⇌ I) |

The compounds of formula (I) are nematic liquid crystalline compounds having weak positive dielectric anisotropy. Accordingly, as a mixture with another nematic liquid crystalline compound having negative dielectric anisotropy, they can be used as a material for a dynamic scattering mode display cell. Also, as a mixture with another nematic liquid crystalline compound having strong positive dielectric anisotropy, they can be used as a material for a field effect mode display cell.

Typical examples of preferred nematic liquid crystalline compounds which can be used in admixture with the compounds of formula (I) include phenyl 4,4'-substituted benzoates, phenyl 4,4'-substituted cyclohexanecarboxylates, biphenyl 4,4'-substituted cyclohexanecarboxylates, 4'-substituted phenyl 4(4-substituted cyclohexanecarbonyloxy)benzoates, 4'-substituted phenyl 4(4-substituted cyclohexyl)benzoates, 4'-substituted cyclohexyl 4(4-substituted cyclohexyl)benzoates, 4,4'-biphenyl, 4,4'-phenylcyclohexane, 4,4'-substituted terphenyl, 4,4'-biphenylcyclohexane, and 2(4'-substituted phenyl)5-substituted pyrimidines.

Table 2 summarizes the viscosities and dielectric anisotropies of mixed liquid crystals composed of 80% by weight of mixed crystals (A) now in widespread use and 20% by weight of compounds Nos. 1 to 5 (n=1) respectively indicated in Table 1. For comparison, the viscosity and dielectric anisotropy of the mixed liquid crystals (A) are also shown in Table 2.

The mixed liquid crystals (A) are composed of and

10% by weight of n-$C_5H_{11}$—⟨⟩—⟨⟩—⟨⟩—CN.

TABLE 2

| | Viscosity (centipoises/20° C.) | Dielectric anisotropy (—) |
|---|---|---|
| (A) | 37.0 | 8.1 |
| (A) + (No. 1) | 30.8 | 7.3 |
| (A) + (No. 2) | 30.9 | 7.3 |
| (A) + (No. 3) | 31.0 | 7.4 |
| (A) + (No. 4) | 31.2 | 7.2 |
| (A) + (No. 5) | 31.3 | 7.3 |

It is seen from the data given in Table 2 that compounds of formula (I) in which n is 1 can reduce the viscosity of the mixed liquid crystals without drastically reducing their dielectric anisotropy.

This effect of the invention will also be clear from a comparative experiment described below.

In order to decrease the viscosity of mixed crystals, each of the following known compounds was mixed with the aforesaid mixed crystals (A) in various proportions.

(No. 15)

and (No. 16)

Likewise, one compound of the invention represented by the following formula (No. 1)

was mixed in various proportions with the mixed liquid crystals (A).

The viscosities and dielectric anisotropies of the three types of mixed liquid crystals obtained were measured.

Figure 1:
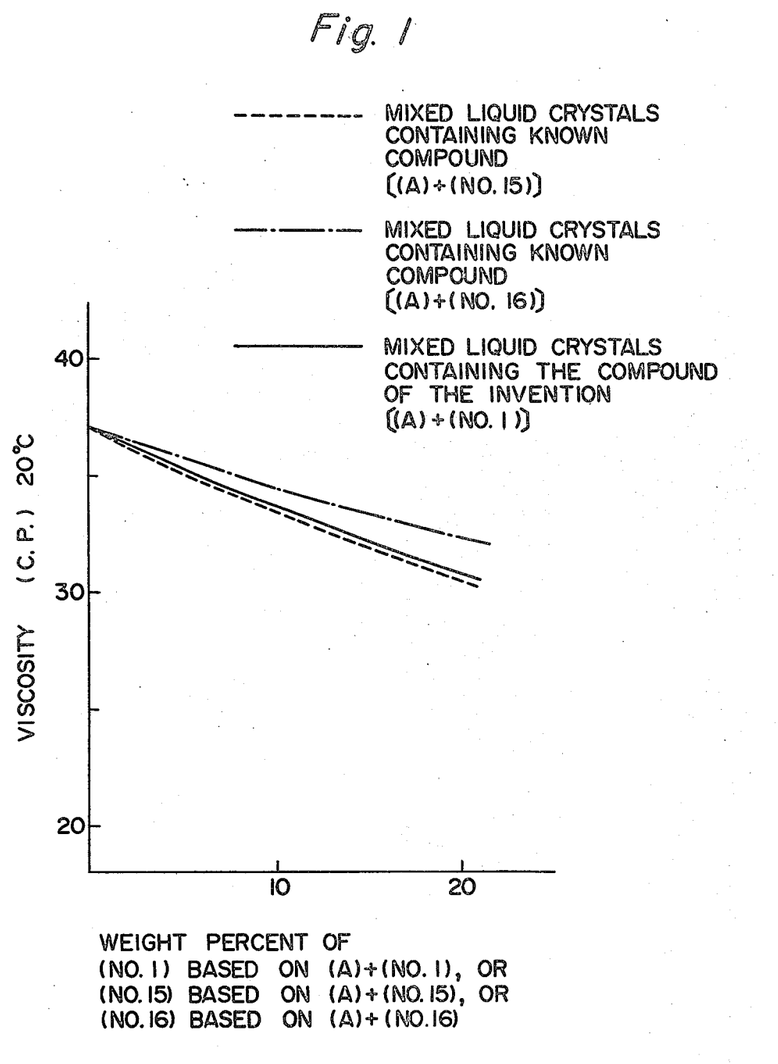
Figure 2:
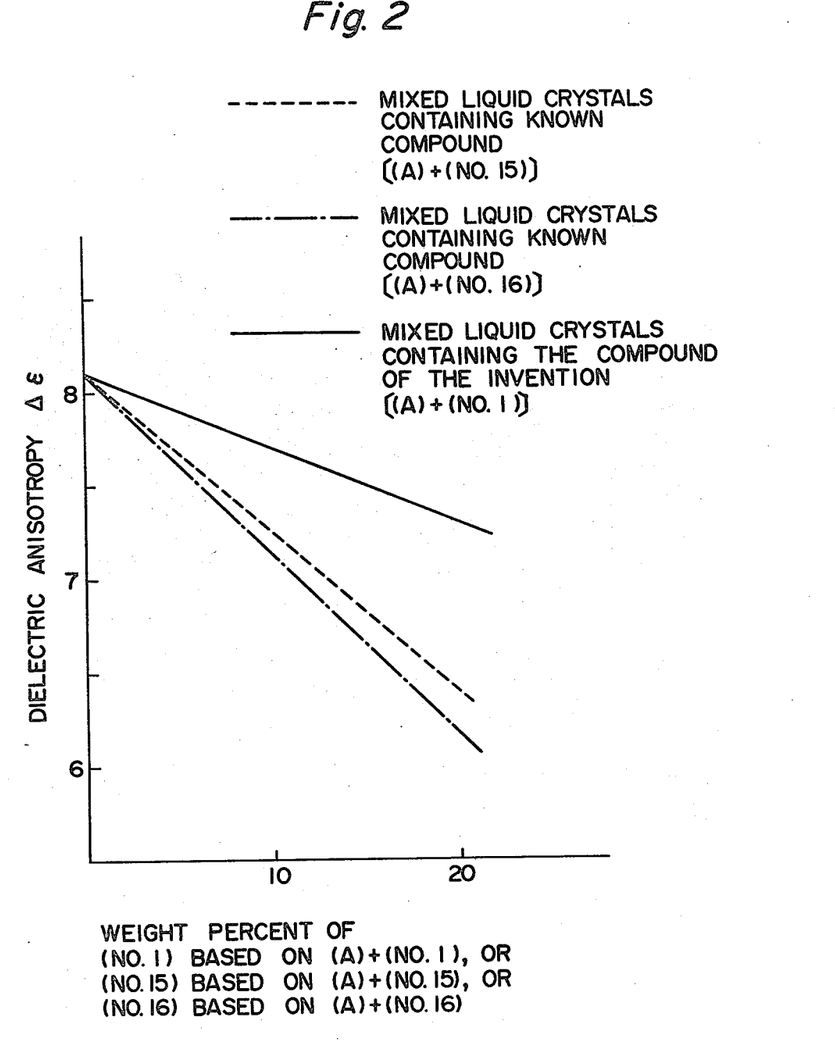
Figure 3:
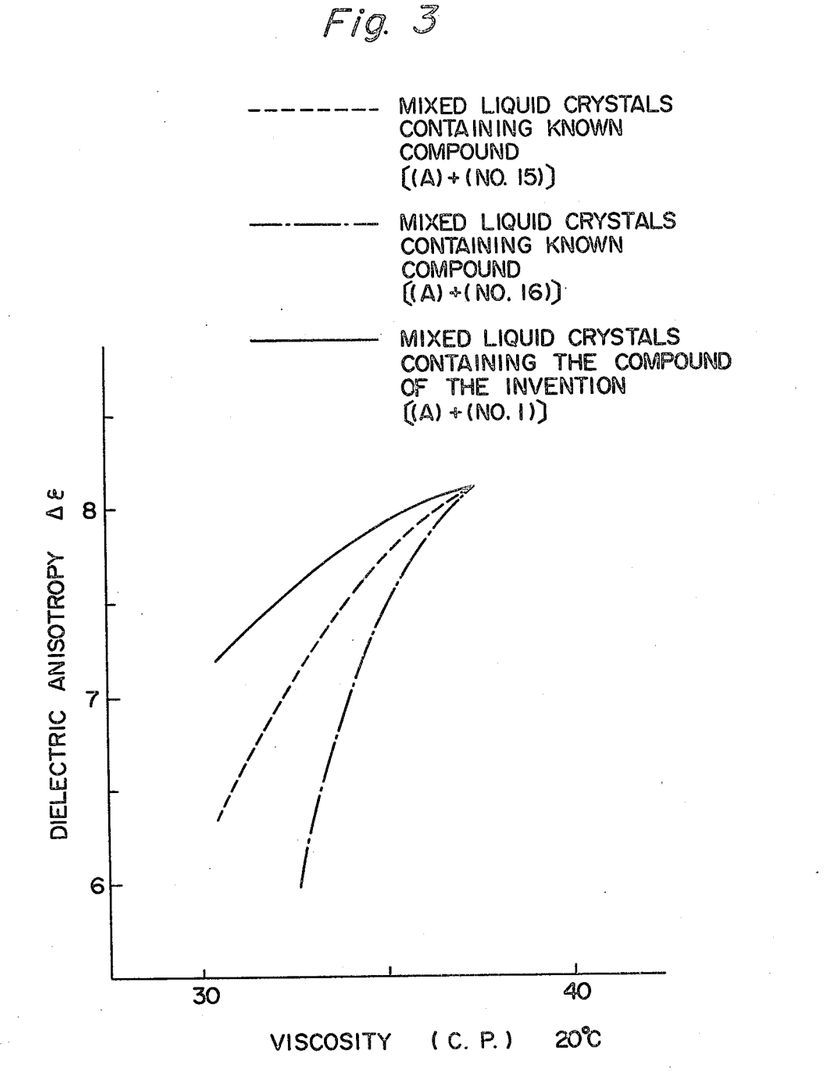

Based on the results of the measurement, the relation between the viscosity and the amount added was plotted in FIG. 1; the relation between the dielectric anisotropy and the amount added, in FIG. 2; and the relation between the dielectric anisotropy and the viscosity, in FIG. 3.

It will be understood from the facts shown in these drawings that the compounds of formula (I) in which n is 1 in accordance with this invention cause a much smaller reduction in dielectric anisotropy with a reduction in viscosity than known compounds used to reduce viscosity.

Table 3 summarizes the N—I points and viscosities of mixed liquid crystals consisting of 80% by weight of matrix liquid crystals (B) now in widespread use as a nematic liquid crystalline material and 20% by weight of compounds Nos. 6 to 14 (n=2) respectively shown in Table 1. For comparison, the N—I point and viscosity of the liquid crystals (B) are also shown in Table 3.

The matrix liquid crystals (B) are composed of

TABLE 3

|  | N-I point (°C.) | Viscosity (centipoises/20° C.) |
|---|---|---|
| (B) | 51.0 | 22.6 |
| (B) + (No. 6) | 60.0 | 22.0 |
| (B) + (No. 7) | 65.7 | 22.0 |
| (B) + (No. 8) | 63.3 | 22.2 |
| (B) + (No. 9) | 65.0 | 22.2 |
| (B) + (No. 10) | 62.6 | 22.4 |
| (B) + (No. 11) | 64.9 | 22.5 |
| (B) + (No. 12) | 72.1 | 24.6 |
| (B) + (No. 13) | 71.2 | 24.9 |
| (B) + (No. 14) | 70.2 | 25.4 |

It will be seen from the data given in Table 3 that the compounds of formula (I) in which n is 2 reduce, or only slightly increase, the viscosity of mixed liquid crystals, and can increase the N—I point of the mixed liquid crystals to a commercially sufficient degree. A viscosity of about 25 centipoises/20° C. is much lower than the viscosities of various mixed liquid crystals having an N—I point of at least 65° C. which are now on an average level of practical utility. The compounds of formula (I) in which n is 2 have a high utilitarian value in that they can give mixed crystals of such a low viscosity.

The effect of this invention will also be clear from a comparative experiment described below.

A known compound of the following formula having a similar chemical structure to the compound of formula (I) in which n is 2 and suitably usable to increase the N—I point of mixed liquid crystals was mixed in various proportions with the matrix liquid crystals (B).

(No. 17)

Likewise, one compound of the invention, (No. 7)

was mixed in various proportions with the matrix liquid crystals (B).

The N—I point and viscosities of the resulting two types of mixed liquid crystals were measured. On the basis of the results of the measurement, the relation between the N—I point and the amount added was plotted in FIG. 4; the relation between the viscosity and the amount added, in FIG. 5; and the relation between the N—I point and the viscosity, in FIG. 6.

Figure 4:
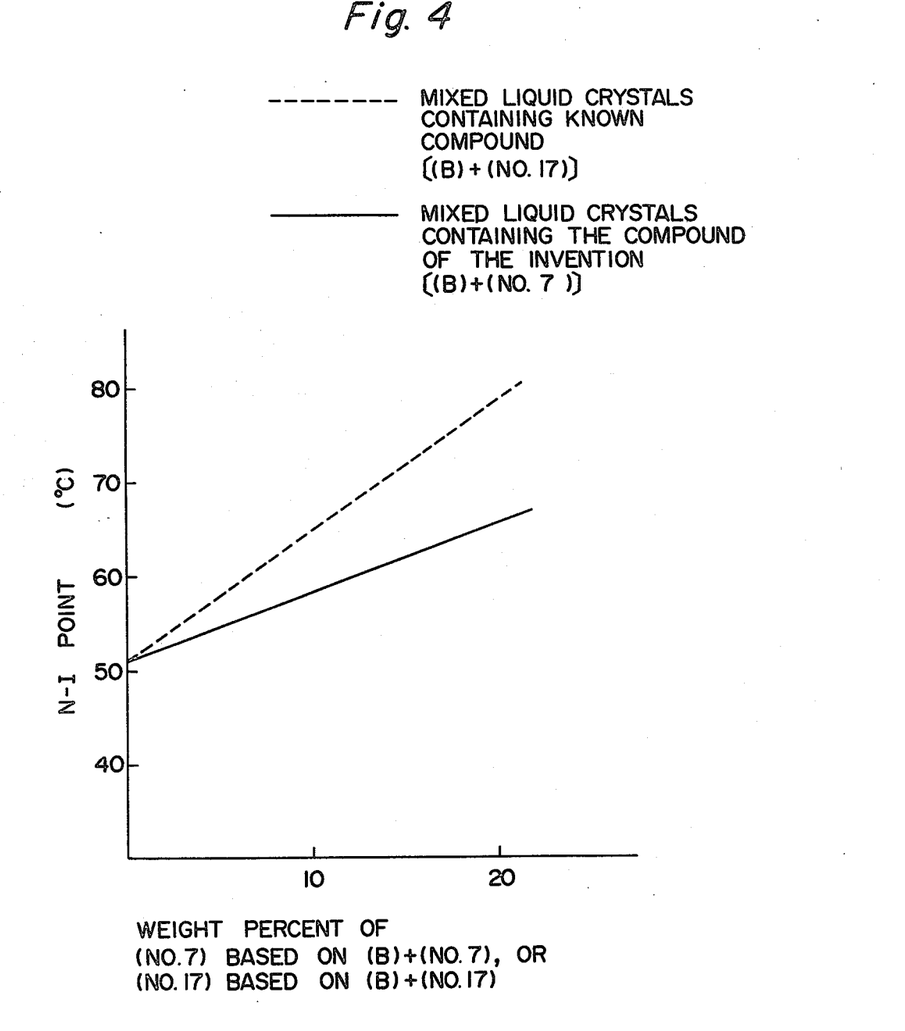
Figure 5:
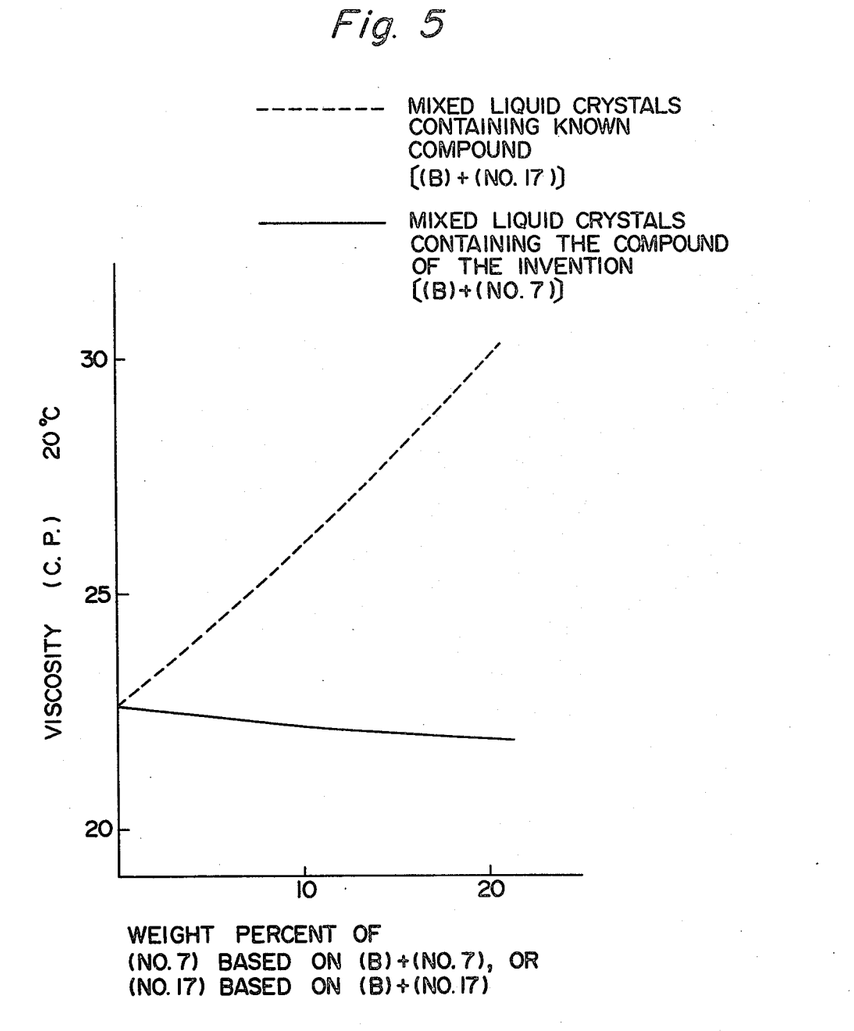
Figure 6:
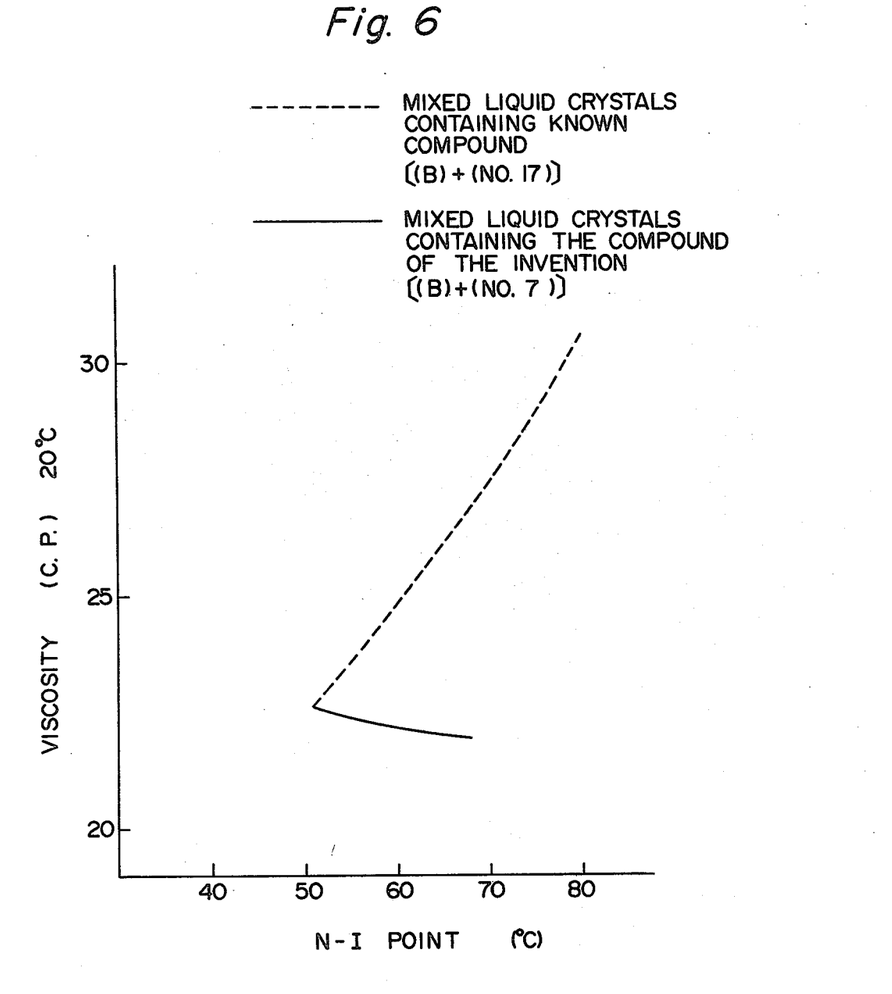

It will be seen from the facts shown in these drawings that the compounds of formula (I) in which n is 2 cause a much smaller increase in viscosity with an increase in N—I point.

The following examples illustrate the represent invention more specifically.

BRIEF DESCRIPTION OF THE DRAWINGS

FIGS. 1–3 show relationships between a property exhibited by a liquid crystalline mixture comprising known composition "A" and adding compound number 1, 15 or 16 disclosed herein. FIG. 1 relates viscosity with amount added; FIG. 2 relates dielectric anisotropy and amount added; FIG. 3 relates dielectric anisotropy with viscosity.

FIGS. 4–6 show property relationships as those above obtained by measuring the properties exhibited by L.C. mixtures comprising known composition "B" and adding compound number 7 or 17.

FIG. 4 relates N—I point with amount added; FIG. 5 relates viscosity with amount added; FIG. 6 relates N—I point with viscosity.

EXAMPLE 1

Anhydrous aluminum chloride (16.0 g; 0.120 mole) was added to 100 ml of carbon disulfide, and with stirring at room temperature, 20.3 g (0.100 mole) of trans-4-n-propylcyclohexylacetyl chloride was added dropwise. The mixture was cooled to 10° C. With stirring, 9.6 g (0.100 mole) of p-fluorobenzene was gradually added dropwise, and reacted at 10° C. for 5 hours and then at room temperature for 2 hours. After distilling off carbon disulfide, the reaction product was added to ice water, and the mixture was stirred at 60° C. for 1 hour. After cooling, the reaction mixture was extracted with ether. The ethereal layer was washed with water and dried. The ether was distilled off, and the residue was distilled under vacuum to give 18.1 g (0.0691 mole) of a compound of the following formula.

To this compound were added 100 ml of triethylene glycol, 12.1 g (0.193 mole) of 80% hydrazine hydride and 22.8 g (0.346 mole) of 85% potassium hydroxide. With stirring, the temperature was gradually raised, and the reaction was carried out at 150° C. for 3 hours. After cooling, 150 ml of water was added, and the mixture was extracted with n-hexane. The extract was washed with water, and dried over anhydrous sodium sulfate. The n-hexane was distilled off, and the residue was distilled under vacuum to give 13.2 g (0.0532 mole; yield 53.2%) of a compound of the following formula.

Transition temperature:    5° C. (C → I)
                          −25° C. (I ⇌ N)

EXAMPLE 2

By operating in the same manner as in Example 1, the following compound was obtained in a yield of 57.1%.

Transition temperature:    9° C. (C → I)
                           −8° C. (I ⇌ N)

EXAMPLE 3

By operating in the same manner as in Example 1, the following compound was obtained in a yield of 53.8%.

Transition temperatures:    7° C. (C → I)
                           −28° C. (I ⇌ N)

EXAMPLE 4

By operating in the same manner as in Example 1, the following compound was obtained in a yield of 56.4%.

Transition temperatures:    12° C. (C → I)
                           −11° C. (I ⇌ N)

EXAMPLE 5

By operating in the same manner as in Example 1, the following compound was obtained in a yield of 55.9%.

Transition temperatures:    13° C. (C → I)
                            −1° C. (I ⇌ N)

EXAMPLE 6

Anhydrous aluminum chloride (16.0 g; 0.120 mole) was added to 100 ml of carbon disulfide, and with stirring at room temperature, 20.3 g (0.100 mole) of trans-4-n-propylcyclohexylacetyl chloride was added dropwise. The mixture was cooled to 10° C., and with stirring, a solution of 18.9 g (0.100 mole) of p-chlorobiphenyl in 30 ml of carbon disulfide was added dropwise. The reaction was carried out at 10° C. for 5 hours and then at room temperature for 2 hours. The reaction mixture, after distilling off carbon disulfide from it, was added to ice water, and the mixture was stirred at 60° C. for 1 hour. After cooling, the mixture was extracted with ether. The ethereal layer was washed with water and dried. The ether was distilled off, and the residue was recrystallized from ethanol to give 23.4 g (0.0660 mole) of the following compound.

Transition temperatures:    143° C. (C → I)
                            137° C. (I ⇌ N)

To this compound were added 200 ml of triethylene glycol, 11.6 g (0.185 mole) of 80% hydrazine hydride and 21.7 g (0.330 mole) of 85% potassium hydroxide. With stirring, the temperature was gradually raised, and the reaction was carried out at 160° C. for 3 hours. After cooling, 300 ml of water was added to the reaction mixture, and the mixture was extracted with benzene. The extract was washed with water, and dried over anhydrous sodium sulfate. Benzene was distilled off, and the residue was recrystallized from n-hexane/ethanol to give 16.6 g (0.0488 mole; yield 48.8%) of the following compound.

-continued

| Transition temperatures: | 100° C. (C ⇌ N) |
| --- | --- |
| | 158° C. (N ⇌ I) |

EXAMPLE 7

Anhydrous aluminum chloride (16.0 g; 0.129 mole) was added to 100 ml of carbon disulfide, and with stirring at room temperature, 20.3 g (0.100 mole) of trans-4-n-propylcyclohexylacetyl chloride was added dropwise. The mixture was cooled to 10° C., and with stirring, a solution of 17.2 g (0.100 mole) of p-fluorobiphenyl in 30 ml of carbon disulfide was added dropwise. The reaction was carried out at 10° C. for 5 hours, and then at room temperature for 2 hours. After distilling off carbon disulfide, the reaction product was added to ice water, and the mixture was stirred at 60° C. for 1 hour. After cooling, the mixture was extracted with ether. The ethereal layer was washed with water and dried. The ether was distilled off, and the residue was recrystallized from ethanol to give 21.6 g (0.0639 mole) of the following compound.

| Transition temperatures: | 108° C. (C → I) |
| --- | --- |
| | 104° C. (I ⇌ N) |

To this compound were added 150 ml of triethylene glycol, 11.2 g (0.179 mole) of 80% hydrazine hydride and 21.0 g (0.320 mole) of 85% potassium hydroxide were added. With stirring, the temperature was gradually raised, and the reaction was performed at 150° C. for 3 hours. After cooling, 200 ml of water was added, and the mixture was extracted with n-hexane. The extract was washed with water, and dried over anhydrous sodium sulfate. The n-hexane was distilled off, and the residue was recrystallized from n-hexane/ethanol to give 16.8 g (0.0520 mole; yield 52.0%) of the following compound.

| Transition temperatures: | 76° C. (C ⇌ N) |
| --- | --- |
| | 125° C. (N ⇌ I) |

EXAMPLE 8

By operating in the same way as in Example 7, the following compound was obtained in a yield of 49.5%.

| Transition temperatures: | 68° C. (C ⇌ N) |
| --- | --- |

-continued

| | 96° C. (N ⇌ I) |
| --- | --- |

EXAMPLE 9

By operating in the same way as in Example 7, the following compound was obtained in a yield of 50.8%.

| Transition temperatures: | 69° C. (C ⇌ N) |
| --- | --- |
| | 113° C. (N ⇌ I) |

EXAMPLE 10

By operating in the same manner as in Example 7, the following compound was obtained in a yield of 55.2%.

| Transition temperatures: | 82° C. (C ⇌ N) |
| --- | --- |
| | 121° C. (N ⇌ I) |

EXAMPLE 11

By operating in the same way as in Example 7, the following compound was obtained in a yield of 52.2%.

| Transition temperatures: | 75° C. (C ⇌ N) |
| --- | --- |
| | 109° C. (N ⇌ I) |

EXAMPLE 12

By operating in the same way as in Example 7, the following compound was obtained in a yield of 53.7%.

| Transition temperatures: | 87° C. (C ⇌ N) |
| --- | --- |
| | 119° C. (N ⇌ I) |

EXAMPLE 13

By operating in the same way as in Example 6, the following compound was obtained in a yield of 54.2%.

| Transition temperatures: | 110° C. (C ⇌ N) |
|---|---|
| | 152° C. (N ⇌ I) |

EXAMPLE 14

By operating in the same way as in Example 6, the following compound was obtained in a yield of 52.9%.

| Transition temperatures: | 114° C. (C ⇌ N) |
|---|---|
| | 147° C. (N ⇌ I) |

What we claim is:

1. A compound of the formula wherein R represents a linear alkyl group having 1 to 7 carbon atoms, n represents an integer of 1 or 2, and X represents F when n is 1 and F or Cl when n is 2.

2. A compound of the following formula:

3. A compound of the following formula:

4. A compound of the following formula:

5. A compound of the following formula:

6. A compound of the following formula:

7. A compound of the following formula:

8. A compound of the following formula:

9. A compound of the following formula:

10. A compound of the following formula:

11. A compound of the following formula:

12. A compound of the following formula:

13. A compound of the following formula:

14. A compound of the following formula:

15. A compound of the following formula:

* * * * *

UNITED STATES PATENT AND TRADEMARK OFFICE
CERTIFICATE OF CORRECTION

PATENT NO. : 4,455,443
DATED : June 19, 1984
INVENTOR(S) : HARUYOSHI TAKATSU, ET AL.

It is certified that error appears in the above—identified patent and that said Letters Patent is hereby corrected as shown below:

On the title page Assignee should read

-- Dainippon Ink and Chemicals, Inc. of Tokyo, Japan --.

Signed and Sealed this

Sixth Day of November 1984

[SEAL]

Attest:

GERALD J. MOSSINGHOFF

Attesting Officer

Commissioner of Patents and Trademarks